(12) United States Patent
Kim

(10) Patent No.: US 11,060,670 B2
(45) Date of Patent: Jul. 13, 2021

(54) LAMP-INTEGRATED GRILLE LIGHTING SYSTEM AND VEHICLE THEREOF

(71) Applicants: HYUNDAI MOTOR COMPANY, Seoul (KR); Kia Motors Corporation, Seoul (KR)

(72) Inventor: Gyu-Bong Kim, Suwon-si (KR)

(73) Assignees: Hyundai Motor Company, Seoul (KR); Kia Motors Corporation, Seoul (KR)

(*) Notice: Subject to any disclaimer, the term of this patent is extended or adjusted under 35 U.S.C. 154(b) by 4 days.

(21) Appl. No.: 16/577,693

(22) Filed: Sep. 20, 2019

(65) Prior Publication Data

US 2020/0109822 A1    Apr. 9, 2020

(30) Foreign Application Priority Data

Oct. 8, 2018    (KR) .................. 10-2018-0119713

(51) Int. Cl.

| F21K 2/06 | (2006.01) |
|---|---|
| F21S 43/13 | (2018.01) |
| F21S 43/20 | (2018.01) |
| F21S 43/19 | (2018.01) |
| F24F 13/10 | (2006.01) |

(Continued)

(52) U.S. Cl.
CPC .............. *F21K 2/06* (2013.01); *C12P 17/167* (2013.01); *F21S 43/13* (2018.01); *F21S 43/195* (2018.01); *F21S 43/26* (2018.01); *F24F 13/10* (2013.01); *B60Q 1/1438* (2013.01); *B60Q 1/18* (2013.01); *B60R 13/005* (2013.01); *F21W 2104/00* (2018.01); *F21Y 2111/00* (2013.01)

(58) Field of Classification Search
CPC . F21K 2/06; F21S 43/13; F21S 43/195; F21S 43/26; C12P 17/167; F24F 13/10; F21W 2104/00; B60Q 1/1438; B60Q 1/18; B60R 13/005; F21Y 2111/00
USPC .......................................................... 362/34
See application file for complete search history.

(56) References Cited

U.S. PATENT DOCUMENTS

| 2004/0086849 A1* | 5/2004 | Shimasaki ........... C12Q 1/6813 435/5 |
| 2009/0185361 A1* | 7/2009 | De Rico Herrero ..... B60Q 1/52 362/34 |

(Continued)

FOREIGN PATENT DOCUMENTS

WO    2004/076231 A2    9/2004

*Primary Examiner* — Rajarshi Chakraborty
*Assistant Examiner* — Hana S Featherly
(74) *Attorney, Agent, or Firm* — Mintz Levin Cohn Ferris Glovsky and Popeo, P.C.; Peter F. Corless

(57) ABSTRACT

A grille lighting system includes a light emitting lamp that includes one or more walls defining an inner space isolated from outside, a light emitting material disposed in the inner space and configured to emit light when the light emitting material contacts air, and a shutter disposed on the one or more walls, wherein the shutter is configured to be opened to allow introduction of outside air to the inner space from outside and further configured to be closed to block introduction of outside air to the inner space. The system further includes a controller configured to control operation of the shutter and cause the shutter to be opened and closed such that when the shutter is opened, the outside air is introduced to contact the light emitting material, which causes the light emitting material to emit light.

18 Claims, 6 Drawing Sheets

(51) Int. Cl.
*C12P 17/16* (2006.01)
*B60Q 1/14* (2006.01)
*F21W 104/00* (2018.01)
*F21Y 111/00* (2016.01)
*B60Q 1/18* (2006.01)
*B60R 13/00* (2006.01)

(56) References Cited

U.S. PATENT DOCUMENTS

2011/0202221 A1\* 8/2011 Sobue ................... B60K 16/00
 701/22
2014/0240468 A1\* 8/2014 Feke ....................... H04N 5/33
 348/47

\* cited by examiner

LAMP-INTEGRATED GRILLE LIGHTING SYSTEM AND VEHICLE THEREOF

CROSS-REFERENCE TO RELATED APPLICATION

This application claims priority to Korean Patent Application No. 10-2018-0119713, filed on Oct. 8, 2018, which is incorporated herein by reference in its entirety.

BACKGROUND

Field

The present disclosure relates to an exterior lamp lighting and more particularly, to a vehicle to which a grille lighting system.

Description of Related Art

Recent trends in vehicle design require the development of a lighting concept that meets the design requirements by extending a lighting area that has remained in an exterior lamp.

For example, a grille lighting may be an example of a lighting concept. The grille lighting implements a lighting design for a front lamp and a radiator grille on the front of the vehicle.

SUMMARY

An aspect of the present invention is to provide a lamp-integrated grille lighting system and a vehicle thereof which extends a lighting area remaining in an exterior lamp to a radiator grille according to recent design requirements to reflect thoroughly recent lighting design requirements, is configured by a bumper integration type lighting lamp particularly using air-contact emissive type bioluminescence or artificial luminescence to minimize an increase in weight for the grille lighting, and overcomes limitations of the lighting area due to package slimness to implement a unique design identity.

Another aspect of the present invention provides a grille lighting system including a light emitting lamp which emits light from a light emitting material externally blocked by coming in contact with outside air and lights a surrounding space by the light due the light emission.

In an embodiment, the light emitting material emits the light by bioluminescence, and the bioluminescence is chemiluminescence by luciferin.

In an embodiment, the light emitting lamp includes a grille illuminator and the grille illuminator generates light by the emission of the light emitting material.

In an embodiment, the grille illuminator is configured by a light emitter placed to an inner space of the connector and the lens coupled to each other, and a shutter that controls blocking of a contact with the outside air for the light emitting material of the light emitter by closing the inner space or the contact with the outside air for the light emitting material by opening the inner space.

In an embodiment, the grille illuminator is configured by a light emitter container, a light emitter cover coupled to the connector to form an inner space covered by the light emitter container, and a shutter that controls blocking of a contact with the outside air for the light emitting material of the light emitter container by closing the inner space or the contact with the outside air for the light emitting material by opening the inner space. The shutter is located at the front surface of the light emitter cover to close or open the inner space.

In an embodiment, the grille illuminator is configured by a light emitter container placed to an inner space of the connector and the lens coupled to each other, and a shutter that controls blocking of a contact with the outside air for the light emitting material of the light emitter container by closing the inner space or the contact with the outside air for the light emitting material by opening the inner space. The shutter is provided in the housing of the connector to close or open the inner space.

In an embodiment, the grille illuminator is configured by a light emitting material coated to an inner space of the connector and the lens coupled to each other, and a shutter that controls blocking of a contact with the outside air for the light emitting material by closing the inner space and the contact with the outside air for the light emitting material by opening the inner space. The light emitting material protrudes from the connector to be coated on a housing coating boss occupying the inner space. The shutter is provided in a lens body of the lens to close or open the inner space.

Further, in order to achieve the objects described above, the present invention provides a vehicle including: a grille lighting system including a light emitting lamp in which light emitted from a light emitting material generated in contact with outside air lights a surrounding space in an inner space by controlling opening and closing; and a radiator grille to which the grille lighting system is applied by forming a grille lighting area.

In an embodiment, the grille lighting system is applied to an emblem in an emblem lighting area formed above the grille lighting area.

In an embodiment, the grille lighting system includes a controller and the controller is associated with a data map in which a table for external illuminance, sunset time, and day/night is constructed to open and close the inner space by outputting a control signal for a camera diaphragm type shutter.

In an embodiment, the controller is associated with an operation button, and the operation button circuit includes into a manual button and an automatic button which transmit a signal to the controller.

The vehicle of the present invention implements the following functions and effects by applying the lamp-integrated grille lighting system.

First, a lighting area remaining in an exterior lamp is extended to a radiator grille portion according to recent design requirements so that vehicle designs reflecting the recent trends are possible. Second, a lamp-integrated structure is possible by using an air-contact emissive type chemical (e.g., luciferin, Mg2+, and ATP) provided inside the lamp. Third, it is easy to adjust lighting/non-lighting by enabling emission control by on/off of the air-contact emissive type chemical. Fourth, by integrating with a front bumper by external lamp integrated structure, it is possible to realize unique design identity by minimizing an increase in weight for grille lighting and overcoming the limitation of the lighting area through package slimness of the lighting. Fifth, it is possible to differentiate lighting concepts not only for autonomous vehicles but also for environmentally friendly vehicles, and it is also possible to respond legally to "an autonomous vehicle display lamp".

DESCRIPTION OF SPECIFIC EMBODIMENTS

Hereinafter, embodiments of the present invention will be described in detail with reference to the accompanying drawings and implemented in various modifications by those skilled in the art as examples, and the present invention is not limited to the embodiments described herein.

A method showing laterally connected image may be implemented by a grille lighting system, in which a separate control lamp in addition to the existing lamp may be required for its implementation. The grille lighting system may emphasize the bilateral connection image while extending the lighting area from the left and right portions of the front lamp toward the radiator grille having light by the control lamp.

Therefore, the mechanical grille lighting system provides a lighting concept that meets some of the recent design requirements.

The control lamp includes a lens, a housing, an inner lens, a light guide, and a fixing bracket like a typical lamp structure. Accordingly, the grille lighting system has limitations of weight and width directional compactness due to the control lamp.

In such a mechanical grille lighting system, it is difficult to sufficiently meet grille lighting design requirements that are being expanded according to recent trends in vehicle lighting area, and in particular, it is difficult to have a structural integrity with respect to the front bumper.

Figure 1:
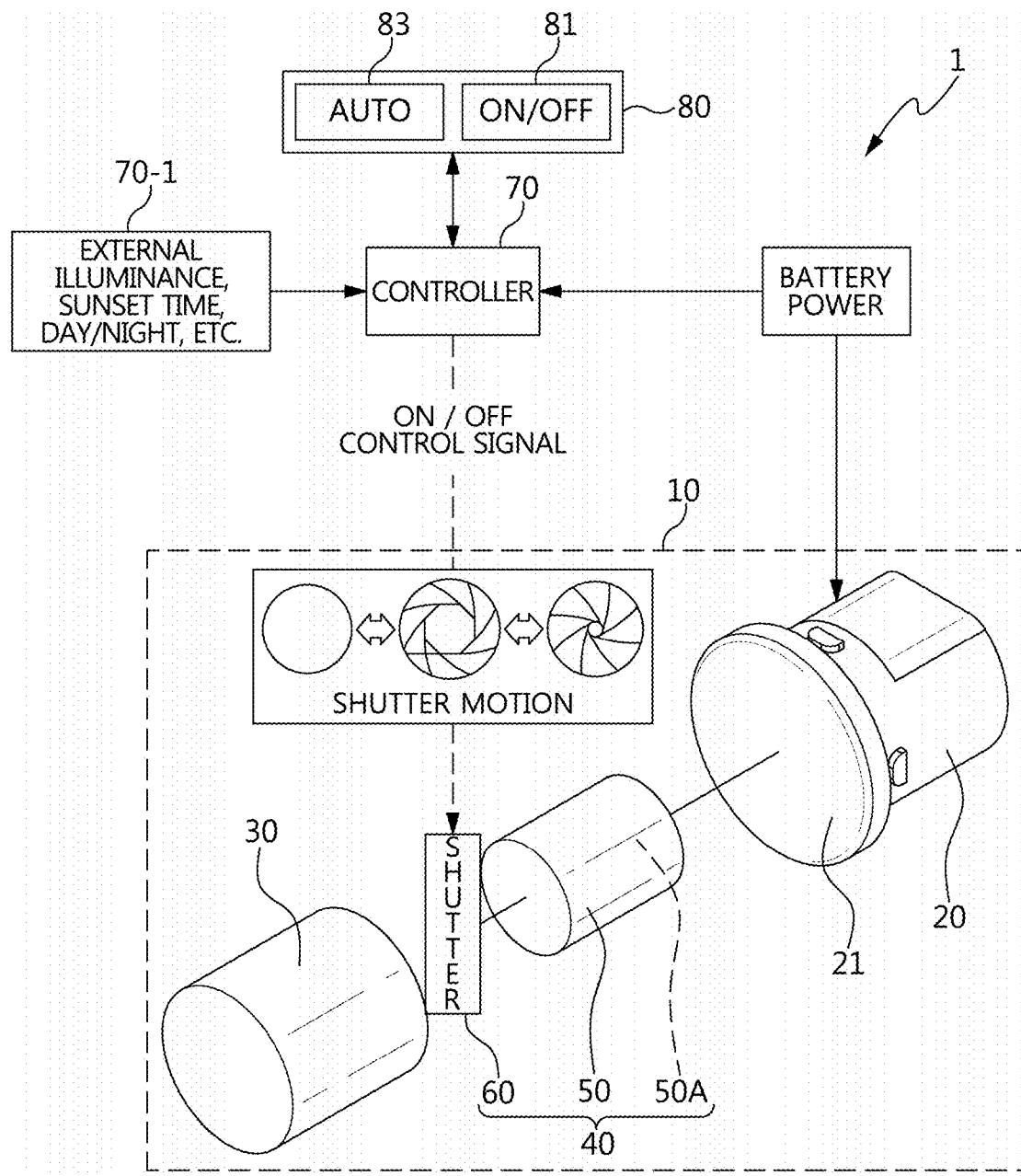
FIG. 1 is a schematic diagram of a lamp-integrated grille lighting system according to the present invention.

Referring to FIG. 1, in an implementation of grille lighting, a grille lighting system 1 includes a light emitting lamp 10, a controller 70, and an operation button circuit 80. In particular, the grille lighting system 1 is referred to as a lamp integrated grille lighting system by using a light emitting material 50A that emits light in contact with outside air in light emission of the light emitting lamp 10.

For example, the following Table 1 illustrates a chemical reaction of the light emitting material 50A.

[Formula 1]

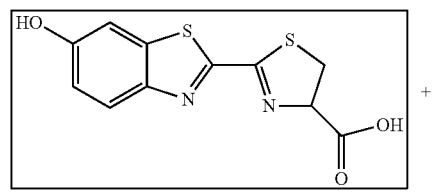

LUCIFERIN (CHEMICAL)

-continued

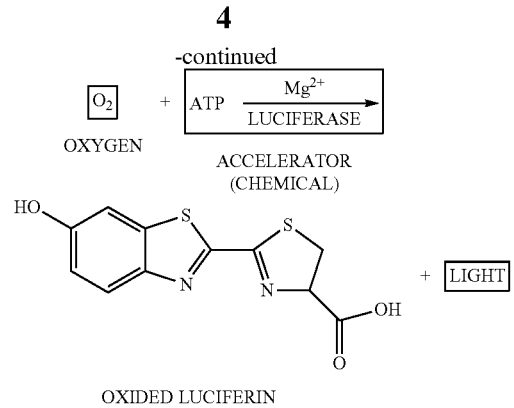

In embodiments, as the light emitting material 50A bioluminescence using chemicals (luciferin, Mg2+, and ATP) having excellent light distribution efficiency by heat loss such as sea creatures and firefly may be used. However, if necessary, artificial luminescence such as luminol, luminescent sticks, fishing floats and the like may also be applied.

For example, the light emitting lamp 10 includes a connector 20, a lens 30, and a grille illuminator 40.

Specifically, the connector 20 has a terminal to which battery power is supplied from the outside. The lens 30 is integrated with the connector 20 to transmit the light emitted from the grille illuminator 40 to the outside through the light emitted from the outside air contact.

Specifically, the grille illuminator 40 includes a light emitter 50 having the light emitting material 50A and a shutter 60. The light emitting material 50A includes bioluminescence using luciferin which emits light by air contact as illustrated in Formula 1. The light emitter 50 is made of a transparent material through which light is transmitted to a storage container containing the light emitting material 50A.

Specifically, the shutter 60 allows outside air to flow toward the light emitter 50 so that the light emitting material 50A comes into contact with the air. For this, the shutter 60 may be operated by a mechanical structure that is opened and closed with power supplied and the power supply may be controlled by the controller 70, but the invention is not limited thereto. The shutter 60 may have a mechanical configuration that does not require electric power. In the present embodiment, since the shutter 60 may include a typical diaphragm shutter that may be used in a camera. The description of a structure and an operation of the diaphragm shutter will be omitted. Also, although the shutter 60 has been described as an example of a camera shutter structure, any one of an automatic door structure in the left/right and up/down direction, a sliding door structure, and a revolving door structure can be applied.

In one implementation, the controller 70 controls the power supply for controlling the opening and closing of the shutter 60, but also controls the power supply to the connector 20 if necessary. Particularly, the controller 70 has a data map 70-1, and the data map 70-1 for detecting and confirming external illuminance, sunset time, and day/night as input information and constructing these input information as a table that is applied to the control of the opening and closing of the shutter 60. In this case, the input information may be acquired by using a light sensor such as an illuminance sensor and a light amount sensor, or confirmed using a timer setting time.

Specifically, the operation button circuit 80 includes a manual button 81 and an automatic button 83. The manual button 81 transmits an ON/OFF signal as an operation signal of the controller 70 by a push button type of setting a driver's press as ON and a driver's release as OFF and in the ON state, the controller 70 outputs a shutter opening/closing signal to the shutter 60. The automatic button 83 automatically outputs the shutter opening/closing signal to the shutter 60 in association with the data map 70-1 of the controller 70.

Figure 2:
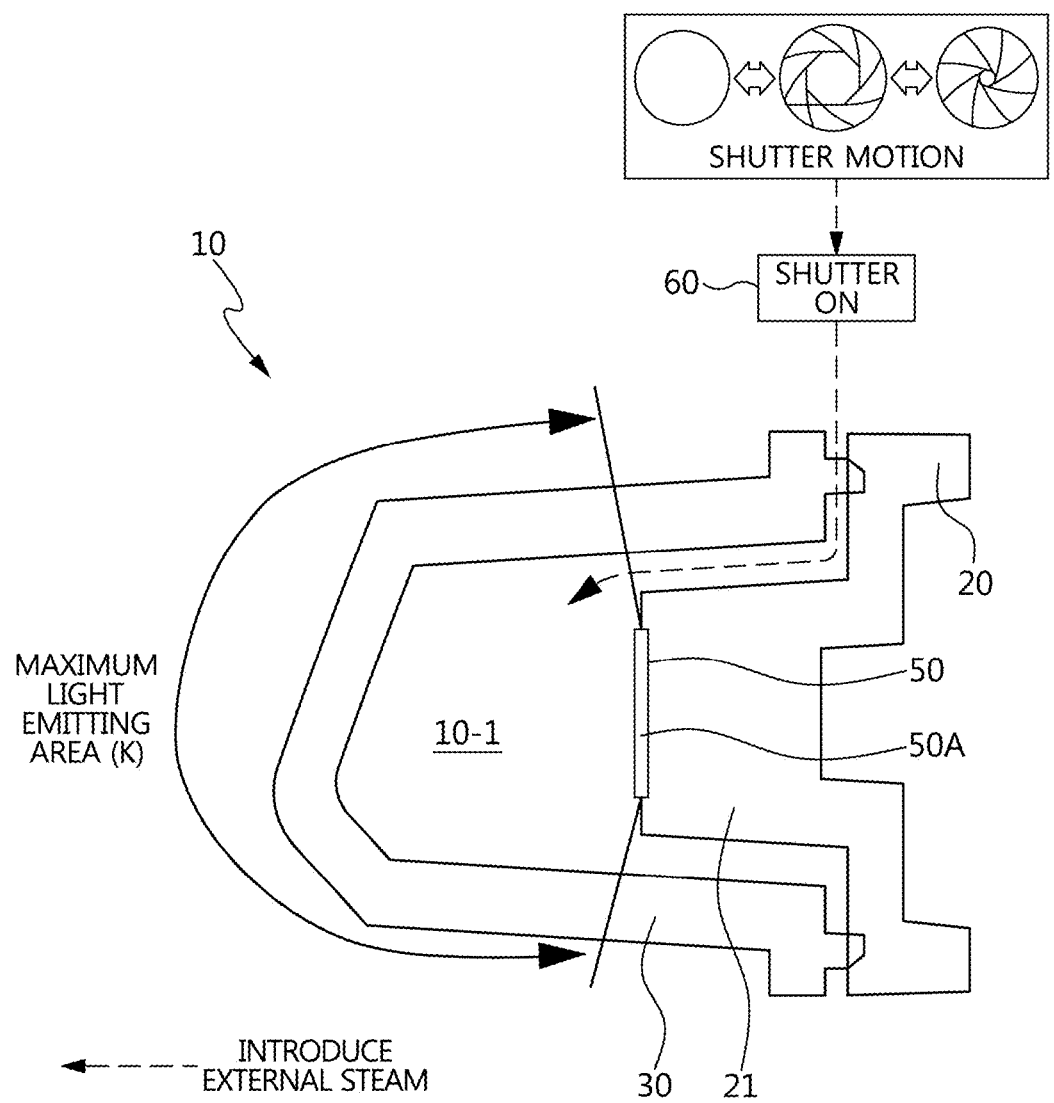
FIG. 2 is a cross-sectional view of an exterior lamp of the lamp-integrated grille lighting system according to the present invention.

In FIG. 2, referring to a cross-sectional view of the light emitting lamp 10, the light emitting lamp 10 forms an inner space 10-1 formed by coupling the connector 20 and the lens 30 to isolate the space 10-1 from outside, and the light emitter 50 is coupled to the connector 20 to be positioned in the inner space 10-1 and the shutter 60 is coupled to the connector 20 or the lens 30 to open or close the inner space 10-1 to the outside.

Particularly, the lens 30 is integrated with the connector 20 using an ultrasonic welding method or a blow molding method (for example, a PET bottle structure) to form the inner space 10-1. The light emitter 50 is fixed to a housing mounting boss 21 of the connector 20 by a fitting or seating structure so that the maximum light emitting area K formed by the light emitting material 50A is formed at about 160° or more. The shutter 60 is coupled to a portion where the connector 20 and the lens 30 are coupled, a housing portion (see FIG. 4) of the connector 20, or a body portion (see FIG. 5) of the lens 30 to allow or block introduction of outside air to the inner space 10-1 by opening and closing.

Figure 3:
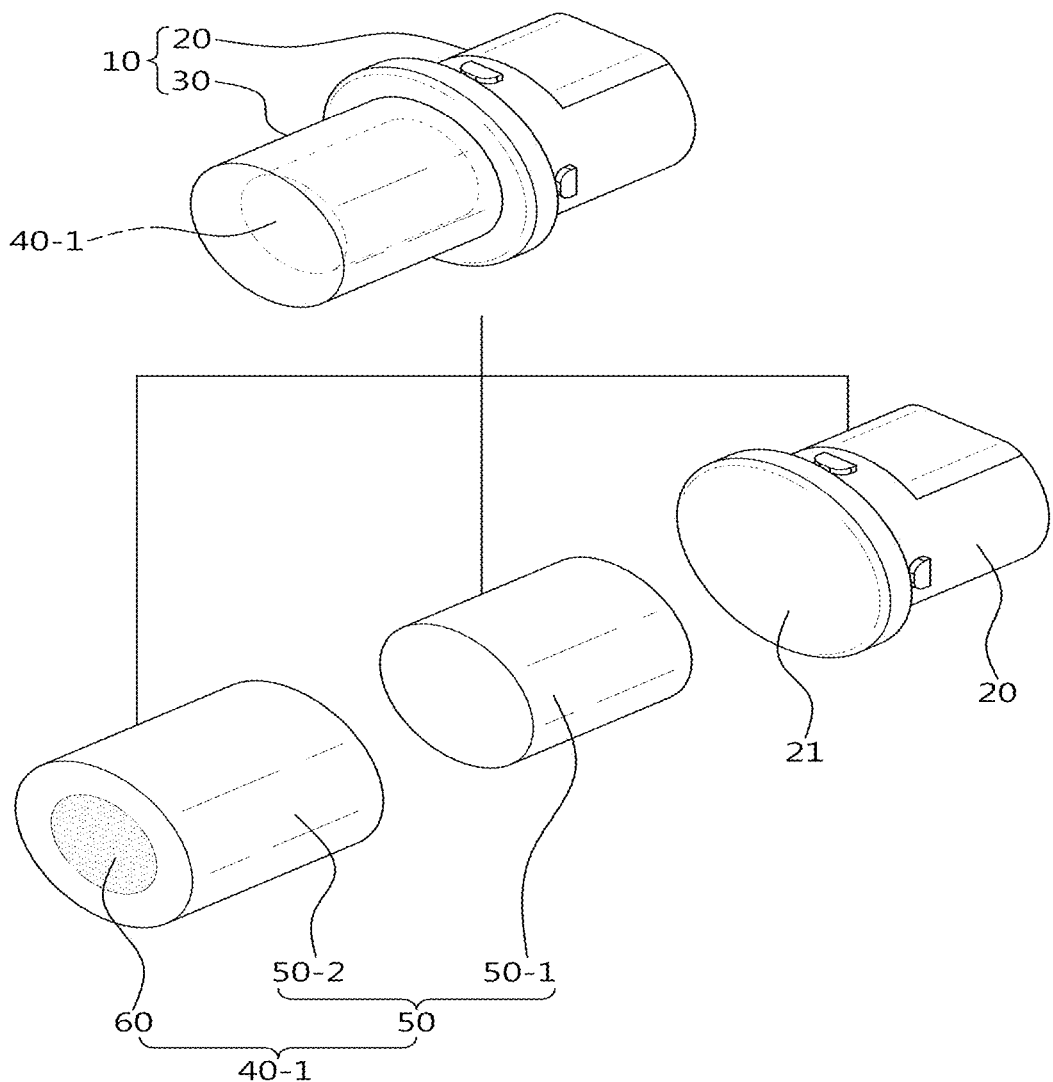
FIG. 3 is an example of configuring a grille illuminator of the exterior lamp according to the present invention as a separated grille illuminator.
Figure 4:
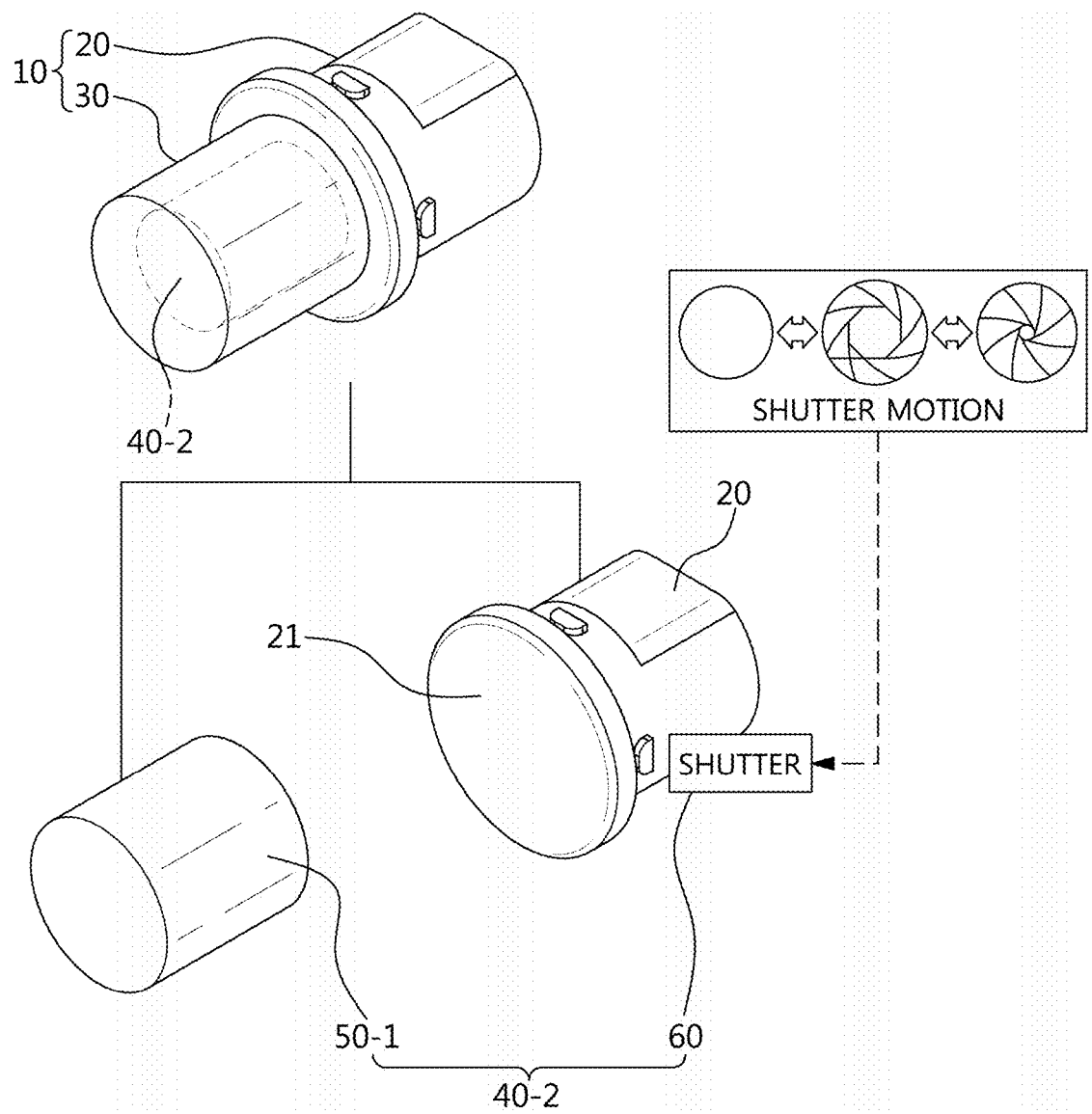
FIG. 4 is an example of configuring a grille illuminator of the exterior lamp according to the present invention as an integrated grille illuminator.
Figure 5:
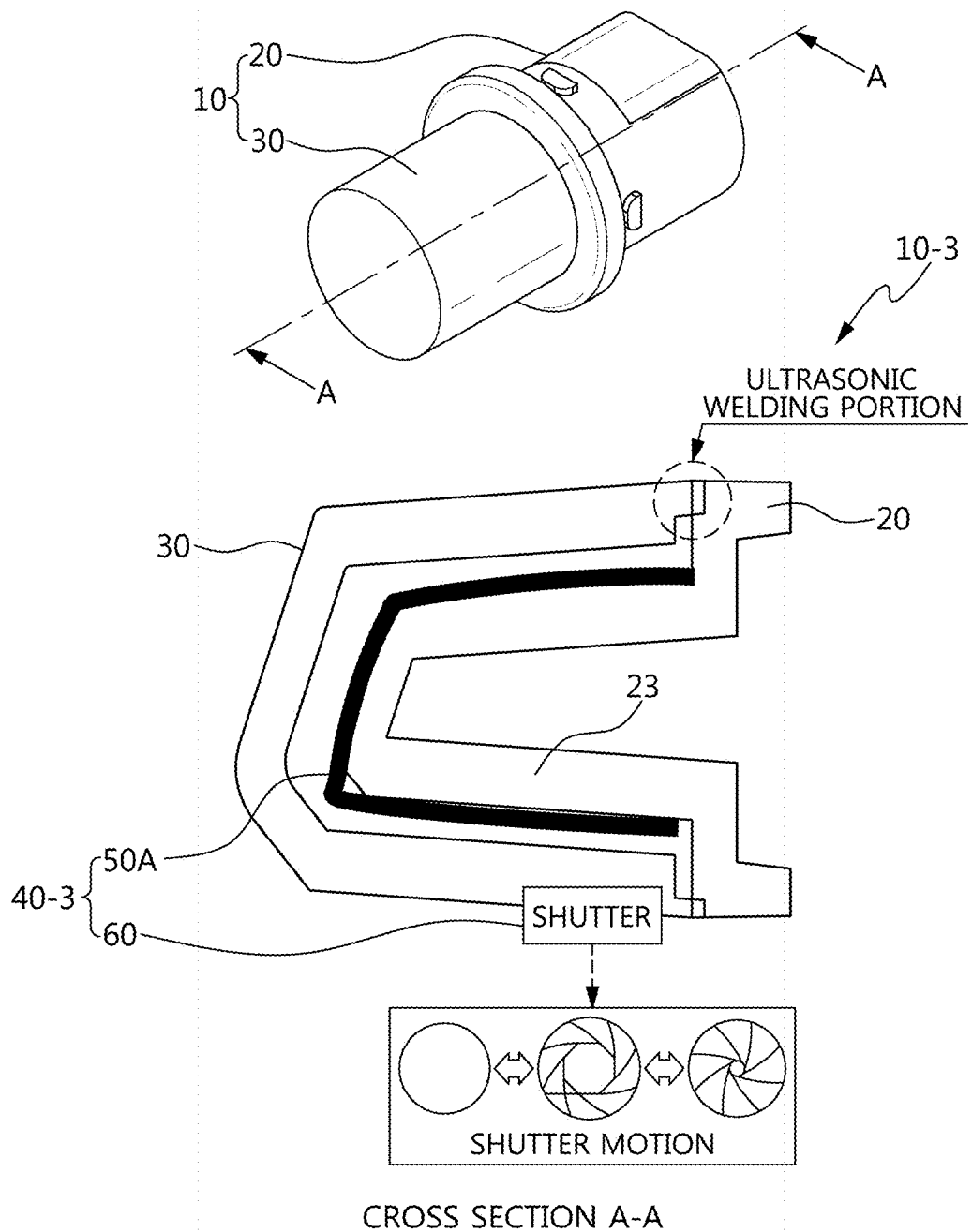
FIG. 5 is an example of configuring a grille illuminator of the exterior lamp according to the present invention as a coated grille illuminator.

Meanwhile, FIGS. 3 to 5 illustrate various examples of the grille illuminator 40 of FIGS. 1 and 2.

Referring to FIG. 3, for example, the grille illuminator may be a separated grille illuminator 40-1 using a light emitter container 50-1, a light emitter cover 50-2, and a shutter 60 is illustrated. In this case, both the light emitter container 50-1 and the light emitter cover 50-2 may be made of a light transmitting material, or only the light emitter cover 50-2 may be made of a light transmitting material.

Particularly, in the separated grille illuminator 40-1, an isolated inner space is formed by the light emitter cover 50-2 and the connector 20.

Specifically, in the separated grille illuminator 40-1, the light emitting material 50A is stored in the light emitter container 50-1 and the shutter 60 is provided in the light emitter cover 50-2. Particularly, in the separated grille illuminator 40-1, the light emitter cover 50-2 covering the light emitter container 50-1 is fixed to the housing mounting boss 21 of the connector 20 by the ultrasonic welding method or the blow molding method and the shutter 60 opens and closes the inner space of the light emitter cover 50-2 at the front portion of the light emitter cover 50-2.

Therefore, in the separated grille illuminator 40-1, while the shutter 60 is closed by the control of the controller 70, the inner space of the light emitter cover 50-2 is shielded from the outside to stop the emission of the light emitting material 50A, but while the shutter 60 is opened by the control of the controller 70, the inner space of the light emitter cover 50-2 communicates with the outside to emit the light from the light emitting material 50A so that the light is projected to the lens 30 through the light emitter container 50-1 and the light emitter cover 50-2.

Referring to FIG. 4, the grille illuminator may be an integrated grille illuminator 40-2 using the light emitter container 50-1 and the shutter 60 is illustrated. In this case, the light emitter container 50-1 is made of a light transmitting material. Particularly, in the integrated grille illuminator 40-2, the lens 30 of the light emitting lamp 10 covers the light emitter container 50-1 to form the inner space 10-1.

Specifically, in the integrated grille illuminator 40-2, the light emitting material is stored in and integrated with the light emitter container 50-1 and the shutter 60 is provided in the housing of the connector 20. Particularly, in the integrated grille illuminator 40-2, the light emitter container 50-1 is fixed to the housing mounting boss 21 of the connector 20 by the ultrasonic welding method or the blow molding method and the shutter 60 opens and closes the inner space of the light emitter container 50-1 at the housing of the connector 20.

Therefore, in the integrated grille illuminator 40-2, while the shutter 60 is closed by the control of the controller 70, the inner space of the light emitter container 50-1 is shielded from the outside to stop the emission of the light emitting material, but while the shutter 60 is opened by the control of the controller 70, the inner space of the light emitter container 50-1 communicates with the outside to emit the light from light emitting material 50A so that the light is projected to the lens 30 through the light emitter container 50-1.

Referring to FIG. 5, the grille illuminator may be a coated grille illuminator 40-3 using the light emitting material 50A and the shutter 60 is illustrated.

Specifically, in the coated grille illuminator 40-3, the light emitting material 50A is directly coated on the housing coating boss 23 having a protruding shape from the connector 20. The shutter 60 is coupled to the body portion of the lens 30 to open and close the connector 20 and the inner space 10-1 of the lens 30. Particularly, the protruding shape of the housing coating boss 23 serves to uniformly spread the light emitted from the light emitting material 50A therearound.

Therefore, in the coated grille illuminator 40-3, while the shutter 60 is closed by the control of the controller 70, the inner space 10-1 is shielded from the outside to stop the emission of the light emitting material 50A, but while the shutter 60 is opened by the control of the controller 70, the inner space 10-1 communicates with the outside to emit the light from the light emitting material 50A so that the light is projected to the lens 30.

Figure 6:
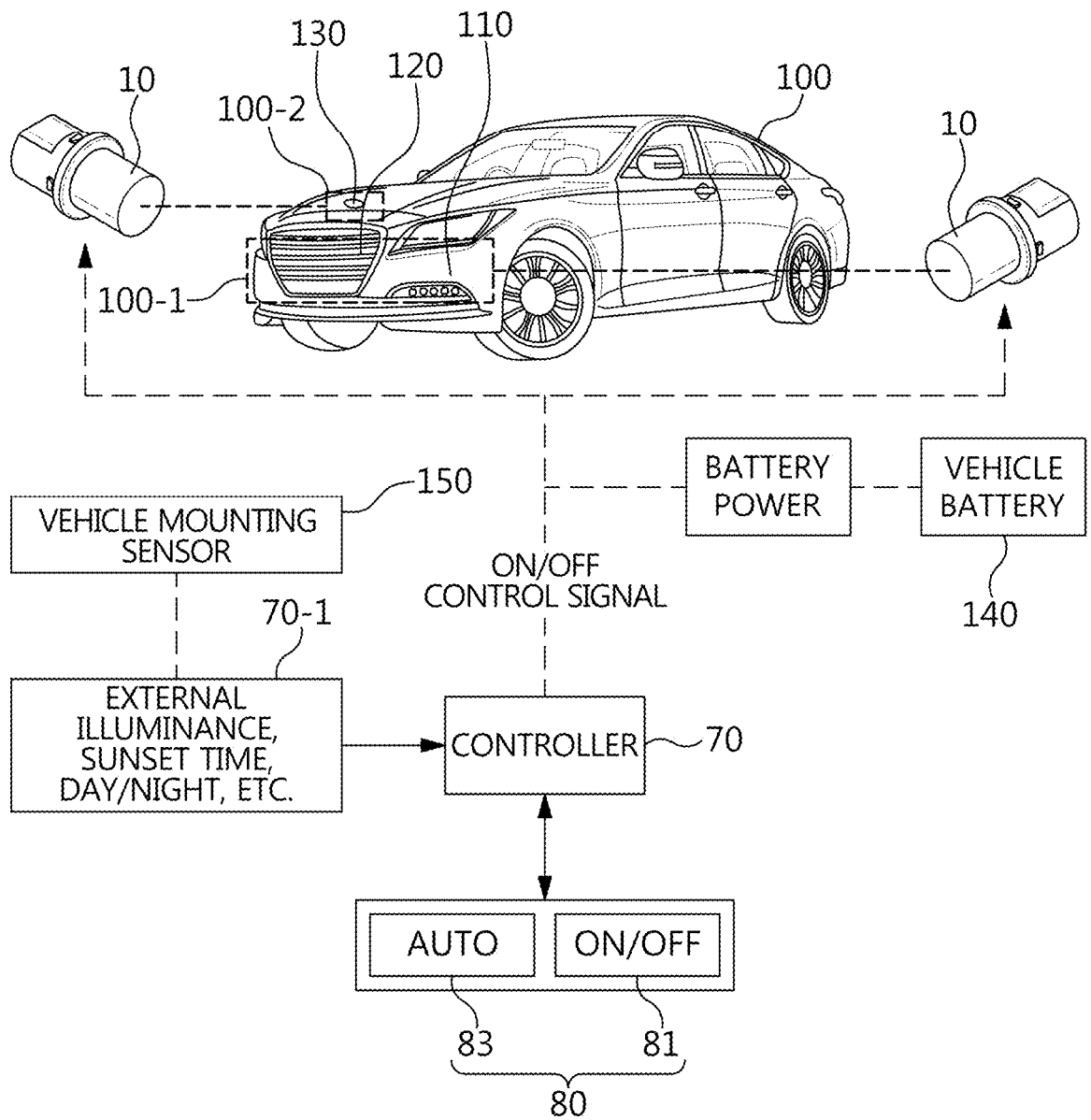
FIG. 6 is an example of a vehicle to which a lamp-integrated grille lighting system according to the present invention is applied.

Meanwhile, FIG. 6 illustrates an example of the vehicle 100 to which the grille lighting system 1 is applied. As illustrated in FIG. 6, the vehicle 100 has a grille lighting system 1 configured by a grille lighting area 100-1 and an emblem lighting area 100-2.

Specifically, the grill lighting system in FIG. 6 may have the same overall system configuration as the grill lighting system 1 shown in FIGS. 1 and 2. The grille illuminator may include the configuration of the separated grille illuminator 40-1 of FIG. 3, the integrated grille illuminator 40-2 of FIG. 4 or the coated grille illuminator 40-3 of FIG. 5. In the grill lighting system 1 shown in FIG. 6, the controller 70 and the shutter 60 receives the power from a vehicle-mounted battery 140 and the data map 70-1 inputs detection information of one or more vehicle sensors.

In embodiments, the vehicle-mounted sensor 150 may be a timer for setting time of the shutter operation. A setting value or a calculation value for the operation of the shutter 60 by the luminance sensor or the light amount sensor or another controller (e.g., an engine controller) is applied to the timer.

Specifically, the grille lighting area 100-1 includes a bumper 110 for buffering shock, and a radiator grille 120 for transmitting outside air toward the radiator of an engine room while forming an outer shape of the front surface of the vehicle. The emblem lighting area 100-2 includes an emblem 130 provided in an engine hood for opening and closing the engine room above the grille lighting area 100-1.

In embodiments, in the vehicle 100, any one of the grille illuminator 40, the separated grille illuminator 40-1, the integrated grille illuminator 40-2, and the coated grille illuminator 40-3 may be used for each of the grille lighting area 100-1 and the emblem lighting area 100-2.

In the vehicle 100, the light emitting material 50A in contact with outside air emits the light by controlling the opening of the shutter 60 of the controller 70 by operating the manual button 81 or the automatic button 83, and the light emitting lamp 10 transmits the light of the light emitting material 50A through the lens 30 and sends the light to the grille lighting area 100-1 and the emblem lighting area 100-2 to thereby illuminate the radiator grille 120 and the emblem 130.

As a result, the vehicle 100 uses the lamp-integrated structure of the grille lighting system 1 to implement structural integrity with the front bumper while satisfying the application of the recent lighting trends and the reflection of the grille lighting design requirements which are not implemented in the existing mechanical grille lighting system.

As described above, the lamp-integrated grille lighting system 1 applied to the vehicle 100 according to the embodiment includes the light emitting lamp 10 that allows the light of the light emitting material 50A to be generated in contact with outside air when the controller causes the shutter to be opened and allow introduction of outside air to the inner space. Particularly, the lamp-integrated grille lighting system 1 is configured by the light emitting lamp 10 integrated with the bumper and using bioluminescence or artificial luminescence, and thus, increase in weight and size for the grille lighting is minimized or avoided.

What is claimed is:

1. A grille lighting system comprising:
    a light emitting lamp comprising:
        one or more walls defining an inner space isolated from outside,
        a light emitting material disposed in the inner space, the light emitting material emitting light by bioluminescence,
        a shutter disposed on the one or more walls, wherein the shutter opens to allow introduction of outside air to the inner space from outside and further closes to block the introduction of outside air to the inner space, and
        a lens and a connector coupled to the lens, wherein the lens and the connector form the one or more walls defining the inner space; and
    a controller configured to control operation of the shutter and cause the shutter to be opened and closed, wherein opening the shutter introduces outside air to contact the light emitting material, which causes the light emitting material to emit light.

2. The grille lighting system of claim 1, wherein the light emitting material is configured to emit the light by bioluminescence.

3. The grille lighting system of claim 2, wherein the light emitting material comprises luciferin.

4. The grille lighting system of claim 1, wherein the light emitting lamp further comprises a grille illuminator that comprises the shutter and the light emitting material.

5. The grille lighting system of claim 1, wherein the light emitting lamp further comprises a light emitter container and a light emitter cover coupled to the connector to form the inner space.

6. The grille lighting system of claim 5, wherein the shutter is provided in the light emitter cover to close or open the inner space.

7. The grille lighting system of claim 6, wherein the shutter is located at the front surface of the light emitter cover.

8. The grille lighting system of claim 1, wherein the light emitting lamp further comprises a light emitter container placed in a space formed by the connector and the lens coupled to each other.

9. The grille lighting system of claim 8, wherein the shutter is provided in a wall of the connector.

10. The grille lighting system of claim 1, wherein the light emitting material is attached to the connector.

11. The grille lighting system of claim 10, wherein the light emitting material is coated on a boss of the connector.

12. The grille lighting system of claim 11, wherein the boss protrudes to the inner space.

13. The grille lighting system of claim 10, wherein the shutter is provided in a lens body of the lens.

14. A vehicle comprising:
    a radiator grille; and
    the grille lighting system of claim 1 attached to the radiator grille and comprising the light emitting lamp for lighting at least a portion of the radiator grille.

15. The vehicle of claim 14, wherein the grille lighting system comprises an additional light emitting lamp for lighting an emblem.

16. The vehicle of claim 14, wherein the grille lighting system comprises the controller.

17. The vehicle of claim 16, wherein the controller includes a data map associated with an output of a control signal to the shutter and the data map constructs a table for external illuminance, sunset time, and day/night.

18. The vehicle of claim 16, further comprising an operation button circuit is configured to transmit a signal to the controller.

* * * * *